(12) United States Patent
Bedell et al.

(10) Patent No.: US 8,092,025 B2
(45) Date of Patent: Jan. 10, 2012

(54) SYSTEM AND METHOD FOR DETECTING CENTRAL RETINAL DISTORTIONS ASSOCIATED WITH MACULAR DISEASES

(75) Inventors: Harold E. Bedell, Houston, TX (US); Jianliang Tong, Houston, TX (US); Stanley Y. Woo, Houston, TX (US)

(73) Assignee: The University of Houston System, Houston, TX (US)

( * ) Notice: Subject to any disclaimer, the term of this patent is extended or adjusted under 35 U.S.C. 154(b) by 206 days.

(21) Appl. No.: 12/660,191

(22) Filed: Feb. 22, 2010

(65) Prior Publication Data

US 2010/0253914 A1 Oct. 7, 2010

Related U.S. Application Data

(62) Division of application No. 11/999,395, filed on Dec. 5, 2007, now Pat. No. 7,806,528.

(60) Provisional application No. 60/873,141, filed on Dec. 6, 2006.

(51) Int. Cl.
 *A61B 3/02* (2006.01)
 *A61B 3/10* (2006.01)
(52) U.S. Cl. ......................................... 351/239; 351/211
(58) Field of Classification Search .................. 351/200, 351/211, 221–223, 237, 239–242, 246; 600/300, 600/558
See application file for complete search history.

*Primary Examiner* — Ricky Mack
*Assistant Examiner* — Mahidere Sahle
(74) *Attorney, Agent, or Firm* — Benjamin A. Adler

(57) ABSTRACT

Provided herein are methods and systems to screen for subjects at risk for retinal-associated eye diseases or to monitor the progression/regression thereof. Generally, the method comprises simultaneously or sequentially displaying to a potentially at-risk individual targets of parallel and nonparallel lines, obtaining an orientation discrimination threshold based on the subject's selections and correlating an increase in the threshold compared to that of a normal control or to a previous threshold measured for the subject as indicative of risk for a retinal-associated eye disease or a progression of the eye disease. Also provided are program storage devices and computer program products effective to store instructions or source code to perform the methods.

30 Claims, 6 Drawing Sheets ated with this invention.

SYSTEM AND METHOD FOR DETECTING CENTRAL RETINAL DISTORTIONS ASSOCIATED WITH MACULAR DISEASES

CROSS-REFERENCE TO RELATED APPLICATIONS

This divisional application claims benefit of priority under 35 U.S.C. §120 of pending nonprovisional application U.S. Ser. No. 11/999,395, filed Dec. 5, 2007 now U.S. Pat. No. 7,806,528, which claims benefit of provisional U.S. Ser. No. 60/873,141, filed Dec. 6, 2006, now abandoned, the entirety of both of which are hereby incorporated by reference.

FEDERAL FUNDING LEGEND

This invention was produced in part using funds obtained through grant NEI T35 EY07088 from the National Eye Institute. Consequently, the federal government has certain rights in this invention.

COMPUTER PROGRAM LISTING APPENDIX

Computer program listings are submitted on compact disc in compliance with 37 C.F.R. §1.96 and are incorporated by reference herein. A total of two (2) compact discs (including duplicates) are submitted herein. The files on each compact disc are listed below:

| Files | Size (KB) | Date Created |
| --- | --- | --- |
| AMDBIG.txt | 8 | Nov. 30, 2007 |
| getrandom.txt | 4 | Nov. 30, 2007 |
| prepare_stimulus_location.txt | 8 | Nov. 30, 2007 |
| presentation_randompermutation | 4 | Nov. 30, 2007 |
| runamdexptbig.txt | 16 | Nov. 30, 2007 |
| settestlinesorientation.txt | 4 | Nov. 30, 2007 |
| TESTAMD.txt | 4 | Nov. 30, 2007 |
| TESTBAR.txt | 4 | Nov. 30, 2007 |
| TESTLINE.txt | 4 | Nov. 30, 2007 |

BACKGROUND OF THE INVENTION

1. Field of the Invention

The present invention relates generally to the fields of optometry, opthalmology and pathologies of the eye. More specifically, the present invention provides a method and system for screening individuals at risk for or having macular degenerative diseases and related central retinal and peripheral retinal conditions to optimize therapeutic interventions.

2. Description of the Related Art

Recent estimates indicate that approximately 8 million Americans have reduced vision as the result of AMD. The prevalence of AMD increases dramatically with age, from approximately 12% of seventy year olds to nearly 25% of people aged 80 or older. Consequently, as the population of the United States ages the total number of afflicted individuals is certain to increase. The vision loss that occurs as the result of AMD has severe adverse consequences for many essential day-to-day activities, such as reading, face recognition, and driving.

Two main forms of AMD are distinguished clinically, i.e., the "dry," atrophic form and the more devastating exudative, or "wet," form. Until a few years ago, exudative AMD was relatively untreatable. However, newly developed medical treatments can slow or even partly restore vision loss to a limited degree (1-2). These treatments require the injection into the vitreous of anti-VEGF agents that retard the growth of new, sub-retinal vessels, which leak fluid into the macula and lead eventually to macular scarring. Because intravitreal injections are uncomfortable for patients, costly, and include a risk of serious complications, substantial current clinical research focuses on determining the appropriate treatment interval and total duration of these injections (3-4). Ideally, the timing of injections should be determined on a patient-by-patient basis with the maximum temporal interval that prevents the accumulation of retinal fluid.

For many years, the Amsler grid was used as a subjective home-monitoring test to alert patients to the possible onset of macular changes. However, the Amsler grid has been shown to be relatively insensitive, as a high proportion of patients with documented visual field losses nevertheless report that the Amsler grid appears to be complete and undistorted (5-7). This is accounted for by perceptual filling-in, whereby the visual system uses information from intact areas of the retina that surround a region of visual field loss to generate a complete and undistorted perception of regular patterns or edges that impinge on the scotoma (8-9). Recently, the PreView PHP was reported to identify perceptual changes associated with the development of choroidal neovascularization in patients with intermediate AMD more accurately than the Amsler grid (10-11). However, this instrument is intended primarily for in-office use by eye-care practitioners or their technical staff.

Thus, there is a recognized need in the art for subject friendly, improved low cost methods of screening for or monitoring the progression of macular degenerative diseases. Specifically, the prior art is deficient in methods of using orientation discrimination thresholds in determining if a subject is at risk for a macular degenerative disease or to monitor the progression thereof in subjects undergoing treatment. The present invention fulfills this long-standing need and desire in the art.

SUMMARY OF THE INVENTION

The present invention is directed to a method of screening for a subject at risk for a retinal-associated eye disease. The method comprises the steps of (a) displaying simultaneously or sequentially at a location on a surface a pair of targets including a first target of a plurality of parallel lines and a second target of a plurality of non-parallel lines to a subject, (b) selecting a target in which the lines appear to be more parallel by the subject, and (c) calculating an orientation discrimination threshold for the subject based on the selection. In step (d) an increase in the orientation discrimination threshold in the subject compared to an orientation discrimination threshold of a control is correlated to a risk for the retinal-associated eye disease in the subject. The control may be a normal control or may comprise a previous orientation threshold measured for the subject. Steps a) to c) may be repeated. In a related method, further steps comprise transmitting the subject's selections over a communication network. In another related method, further steps comprise transmitting over the communication network times at which the subject performs the steps a) to c). In yet another related method, further steps comprise sending a reminder to the subject to perform the steps a) to c) as instructed by an eye care provider. In yet another related method, further steps comprise examining the subject's eye by the eye care provider, diagnosing a retinal-associated eye disease in the subject and determining a therapeutic intervention for the disease. In yet another related method, further steps comprise monitoring progression or regression of the retinal-associated eye disease and optimizing the therapeutic intervention based on the progression/regression thereof.

The present invention also is directed to a system for screening for a retinal-associated eye disease in a subject. The system comprises a surface configured to display simultaneously or sequentially at a location thereon a pair of targets including a first target of a plurality of parallel lines and a second target of a plurality of non-parallel lines to a subject, a memory and a processor connected to the memory and configured to perform the method steps for screening for a macular degenerative disease in a subject as described herein.

The present invention is directed further to a program storage device. The program storage device is readable by an electronic medium and tangibly stores instructions executable by the electronic medium to perform the steps for screening for a retinal-associated eye disease in a subject as described herein.

The present invention is directed further still to computer program product comprising a computer useable medium that tangibly stores as computer readable code the method for screening for a retinal-associated eye disease in a subject as described herein.

Other and further aspects, features and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

In FIG. 2A a patch of lines with variable orientations is on the 90-deg meridian and a patch of parallel lines is on the 270-deg meridian. In FIG. 2B a patch of lines with variable orientations is on the 45-deg meridian and a patch of parallel lines is on the 225-deg meridian. In FIG. 2C a patch of lines with variable orientations is on the 135-deg meridian and a patch of parallel lines is on the 315-deg meridian. In FIG. 2D a patch of lines with variable orientations is on the 0-deg meridian and a patch of parallel lines is on the 180-deg meridian.

DETAILED DESCRIPTION OF THE INVENTION

Figure 1A:
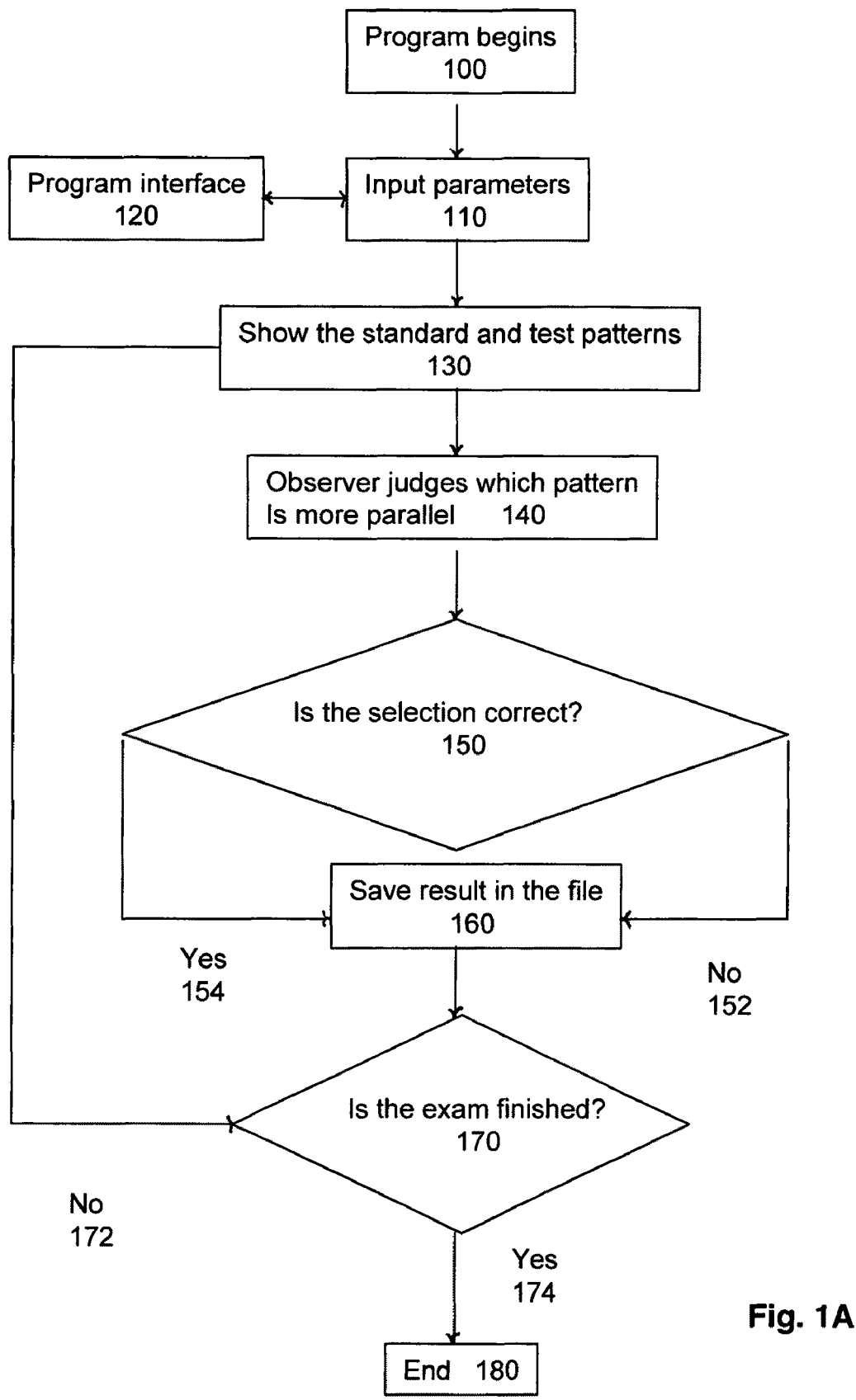
FIGS. 1A-1B depict a flow chart of the method used to screen for AMD (FIG. 1A) and the program interface for the screening test (FIG. 1B).

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the term "subject" refers to any recipient of the screening test.

In one embodiment of the present invention there is provided a method of screening for a subject at-risk for a retinal-associated eye disease, comprising: (a) displaying at a location on a surface a pair of targets including a first target of a plurality of parallel lines and a second target of a plurality of non-parallel lines to a subject; (b) selecting a target in which the lines appear to be more parallel by the subject; (c) calculating an orientation discrimination threshold for the subject based on the selection; and (d) correlating an increase in the orientation discrimination threshold in the subject compared to an orientation discrimination threshold of a control as indicating a risk for the retinal-associated eye disease in the subject. In this embodiment the steps (a) to (c) may be repeated.

Further to this embodiment the method may comprise transmitting the subject's selections over a communication network. In this further embodiment the transmissions may be in real time.

In another further embodiment the method may comprise transmitting the subject's selections over a communication network in real time to an eye care provider. Further to this embodiment the method may comprise examining the subject's eye by the eye care provider; diagnosing a retinal-associated eye disease in the individual; and determining a therapeutic intervention for the disease. Further still to this embodiment the method may comprise repeating steps (a) to (c); monitoring progression or regression of the retinal-associated eye disease; and optimizing the therapeutic intervention based on the progression or regression thereof.

In yet another further embodiment the method may comprise transmitting over the communication network times at which the subject performs the steps (a) to (c).

In yet another further embodiment the method may comprise sending a reminder to the subject to perform the steps (a) to (c) as instructed by an eye care provider.

In all embodiments of this method the surface comprises a computer monitor screen, a screen on a cellular phone, a screen on a PDA or a screen on a self-contained electronic device. Also, the control may be a normal control comprising a normative database of orientation discrimination thresholds determined for normal eyes or may comprise previous thresholds measured for the subject. In addition, the targets may be displayed simultaneously or sequentially and, also, the targets may be displayed for 200 ms or less. The targets also may be displayed on the surface at 8 visual-field locations adjacent to a central fixation stimulus. Alternatively, the targets may be displayed centered within a same central region of a visual-field such that fixation is directed between a set of 4 peripherally located brackets. Furthermore, the lines may be about 0.2 deg to about 0.6 deg in length.

Also, in all embodiments the retinal-associated eye disease may be a disease of the macula, of the central retina or of the peripheral retina. Examples of the retinal-associated eye disease may be early age-related macular degeneration, diabetic macular edema, hereditary macular dystrophy, drug-related macular dystrophy, hereditary peripheral retinal degenerations, pigmentary retinopathy, or cystoid macular edema.

In another embodiment of the present invention there is provided a system for screening for a retinal-associated eye disease in a subject, comprising: a surface configured to display at a location thereon a pair of targets including a first target of a plurality of parallel lines and a second target of a plurality of non-parallel lines to a subject; a memory; and a processor connected to the memory and configured to perform the steps of: (a) displaying at a location on a surface a pair of targets including a first target of a plurality of parallel lines and a second target of a plurality of non-parallel lines to a subject; (b) selecting a target in which the lines appear to be more parallel by the subject; (c) calculating an orientation discrimination threshold for the subject based on the selections; and (d) correlating an increase in the orientation discrimination threshold in the subject compared to an orientation discrimination threshold of a control. In all embodiments the first target and the second target may be displayed simultaneously or sequentially.

Further to this embodiment the system may comprise one or both of a normative database of orientation discrimination thresholds as the normal control or a listing of previous thresholds measured for the subject stored in the memory.

In another further embodiment the system may comprise a communication network connection, where the processor is configured to perform further steps of transmitting the subject's selections to another processor. In this further embodiment the transmissions may be in real time. Also, the subject's selections may be transmitted to an eye care provider in real time.

In yet another further embodiment the system may comprise a communication network connection, where the processor is configured to perform further steps of transmitting times at which the subject performs the steps (a) to (c) to another processor.

In yet another further embodiment the system may comprise a communication network connection, wherein the processor is configured to perform further steps of receiving a reminder for the subject to perform steps (a) to (c) as instructed by an eye care provider.

In yet another embodiment of the present invention there is provided a program storage device readable by an electronic medium and tangibly storing instructions executable by the electronic medium to perform the steps for screening for a retinal-associated eye disease in a subject, comprising (a) displaying simultaneously at a location on a surface a pair of targets including a first target of a plurality of parallel lines and a second target of a plurality of non-parallel lines to a subject; (b) selecting a target in which the lines appear more to be parallel by the subject; (c) calculating an orientation discrimination threshold for the subject based on the selections; and (d) correlating an increase in the orientation discrimination threshold in the subject compared to an orientation discrimination threshold of a control. The electronic medium may be a computer, a cellular phone, a PDA or a self-contained electronic device. In all embodiments, the first target and the second target may be displayed simultaneously or sequentially.

Further to this embodiment the program storage device further one or both of a normative database of orientation discrimination thresholds as the normal control or a listing of previous thresholds measured for the subject as the control.

In another further embodiment the executable instructions may perform the steps of transmitting the subject's selections to another electronic medium. In this further embodiment the transmissions may be in real time.

In yet another further embodiment the executable instructions may perform the steps of transmitting times at which the subject performs the steps (a) to (c) to another electronic medium.

In yet another further embodiment the executable instructions may perform the steps of sending a reminder to the subject to perform the steps (a) to (c) as instructed by an eye care provider.

In yet another embodiment of the present invention there is provided a computer program product comprising a computer useable medium that tangibly stores as computer readable code instructions to perform the method for screening for a retinal-associated eye disease in a subject as described supra.

Provided herein are systems and methods for allowing subjects who are at risk for developing or have age-related macular disease and other forms of central- or -peripheral vision loss to monitor their status regularly at home. The design of the method makes it substantially more sensitive than current home-monitoring tests. Implementation uses personal electronic devices which are almost universally available. This form of implementation makes the method available to virtually all at-risk individuals, i.e., primarily those over 50 years of age, at low cost.

In prior art testing methods perceived distortions that are expected from disruption of the retinal photoreceptor layer are reduced by a cortical filling in process. Using randomly-arrayed instead of regularly-spaced stimuli should minimize filling in, making the expected perceptual distortions more readily detectable. Thresholds to discriminate variability in line orientation are predicted to be elevated in subjects with early AMD, for example. Also, insensitivity to orientation variability is predicted to correlate spatially with areas of observable macular changes, e.g., drusen. In addition thresholds are expected to increase further as the disease process progresses.

The screening methods or tests or systems comprising the same may be used primarily for home monitoring by those at risk for developing age-related macular degeneration and related macular diseases or other central and peripheral retinal conditions or disorders. Alternatively, the method may be used by optometrists and ophthalmologists for in-office testing of central visual status and should be available in optometrists' and ophthalmologists' offices for vision testing and for patient education.

As provided herein, the screening method or test uses randomly positioned short line segments, such as, but not limited to, segments longer than 0.2 deg and shorter than 0.6 deg in length, to evaluate the physiological status of the central visual field in subjects at risk for macular disease. The line targets that are used are relatively insensitive to blur or other optical degradation that may be present in older eyes. The subject compares the variability in orientation between two groups of lines that are presented simultaneously or sequentially. This forced-choice procedure ensures that the screening method assesses optimal sensitivity and is unaffected by criterion effects.

The screening method presents groups of targets on opposite sides of a fixation stimulus for a duration of 200 ms or less. The brief duration and the presentation of targets on opposite sides of the fixation target prevent systematic errors in the retinal locations of the targets, which could be induced by eye movements made by the subject. The method presents groups of targets in 8 visual-field locations or meridians adjacent to a central fixation stimulus. Comparison of the subject's responses for targets in these 8 locations allow the method to localize regions of visual-field and retinal disturbance. Alternatively, particularly with sequential presentation, the groups of targets may be presented centered within the same 4-deg central region of the visual field where fixation is directed between a set of 4 peripherally located brackets.

The briefly flashed targets may be random lines, dotted lines or groups of dots that form simple shapes, such as circles, squares, triangles, etc. For example, targets may comprise, although not limited to, 8 or 10 lines per group. Lines or dot targets may be presented centrally, para-centrally or peripherally to detect different ocular conditions, such as, macular degeneration vs. peripheral photoreceptor degenerations. Variations on the screening test, such as, but not limited to, larger targets flashed at more eccentric retinal locations, may be used to detect diseases and degenerations of non-central retinal, e.g. retinitis pigmentosa and others.

Implementation of the method using computer monitors or the screen of widely used personal electronic devices, for example, cell phones, PDAs, self-contained or stand-alone electronic devices, etc., allows the test to be performed routinely outside of a clinical office setting. Because subjects keep their cell phones and PDAs and other self-contained or stand-alone electronic devices with them virtually all the time, this form of implementation is ideal for home monitoring. The implementation of the method on widely available personal electronic devices renders it relatively inexpensive and therefore available to the large numbers of older subjects who are at risk for macular degeneration.

Storing test results on the subjects' personal electronic devices allows clinicians to monitor each subject's compliance in performing the prescribed home screening test. In addition, sequential test results can be downloaded to the subjects' clinical file when the subject has an appointment with his eye-care provider. Alternatively, if a cell phone is used, it can transmit automatically the data to the subject's eye care provider after each test. Eye-care providers can thereby closely monitor the changes in test results over time. Another advantage of using a cell phone or similar electronic device for the test is that the device can be programmed to remind the subject to complete the test at scheduled times. Just as a cell phone can automatically transmit test results to eye-care providers, it can alert subjects to make an appointment or even make the appointment automatically if results fall outside the normal range.

As shown in FIG. 1A, the screening method begins with a computer program or computer program product 100. At step 110 input parameters, such as subject information and stimulus parameters, are entered into the program interface 120. The standard and test patterns are shown to the subject at step 130. The subject, as observer, judges which pattern is more parallel at step 140. Whether the judgment is incorrect, i.e., no 152, or correct, i.e., yes 154, is determined at step 150 and the result for either judgment is saved in the subject's file at step 160. At step 170 a determination is made whether the examination is finished. If no 172, the method returns to step 130. If yes 174, the program ends at step 180.

Figure 1B:
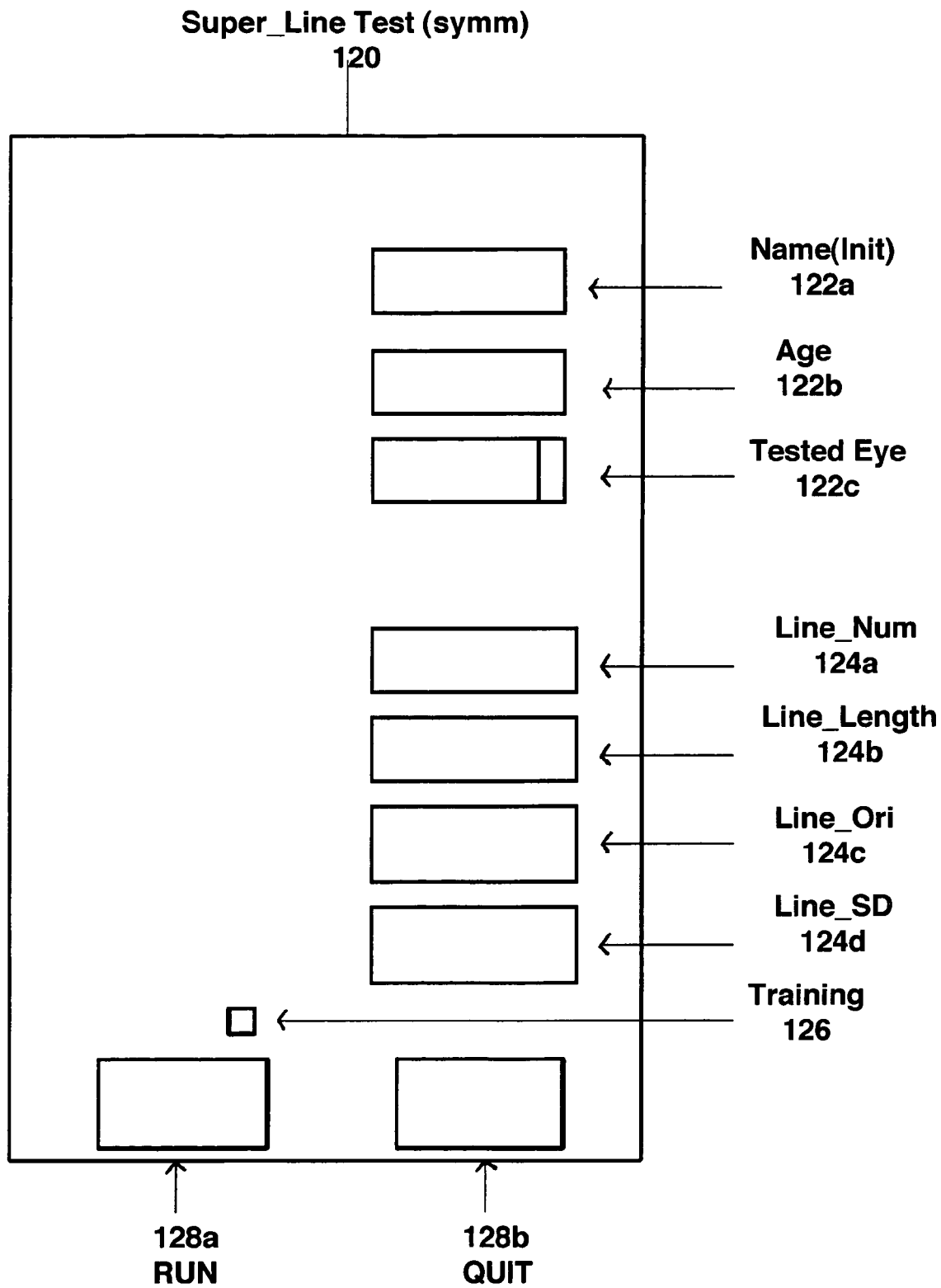
Figure 2A:
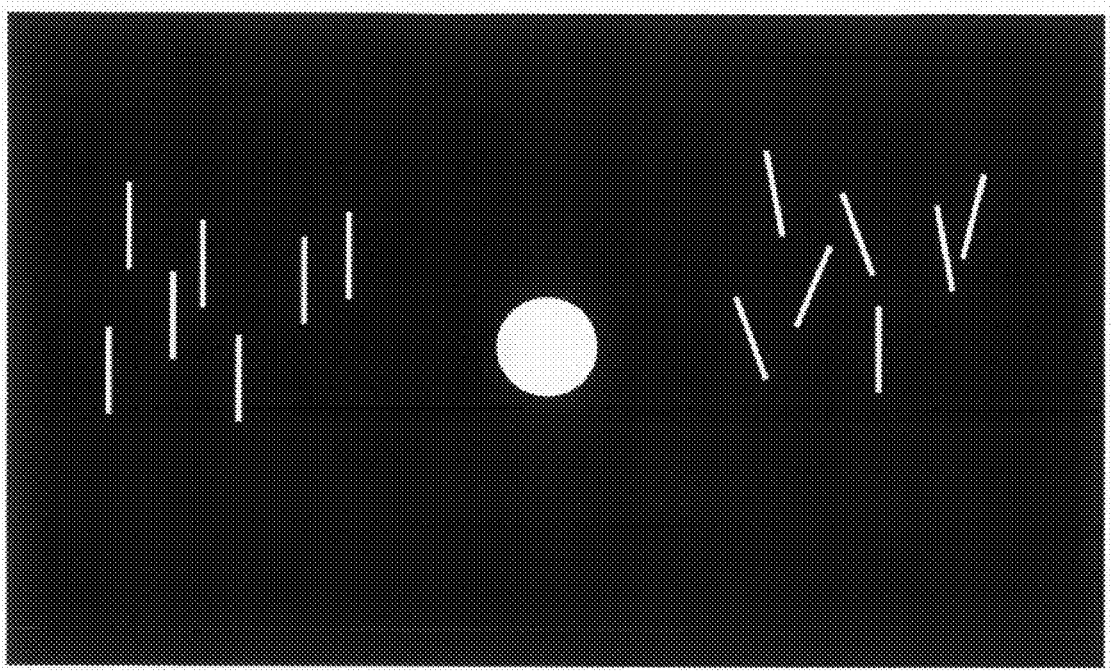
FIGS. 2A-2D depict targets with randomly positioned lines used to assess orientation discrimination when presented simultaneously.
Figure 2B:
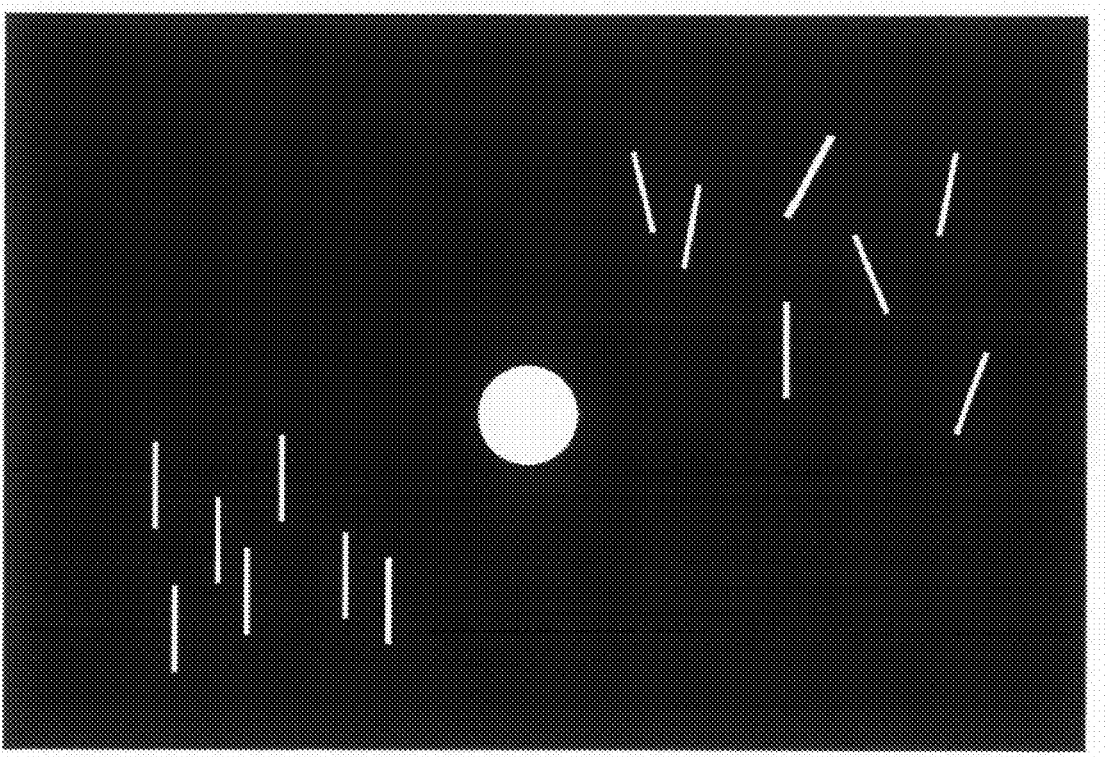
Figure 2C:
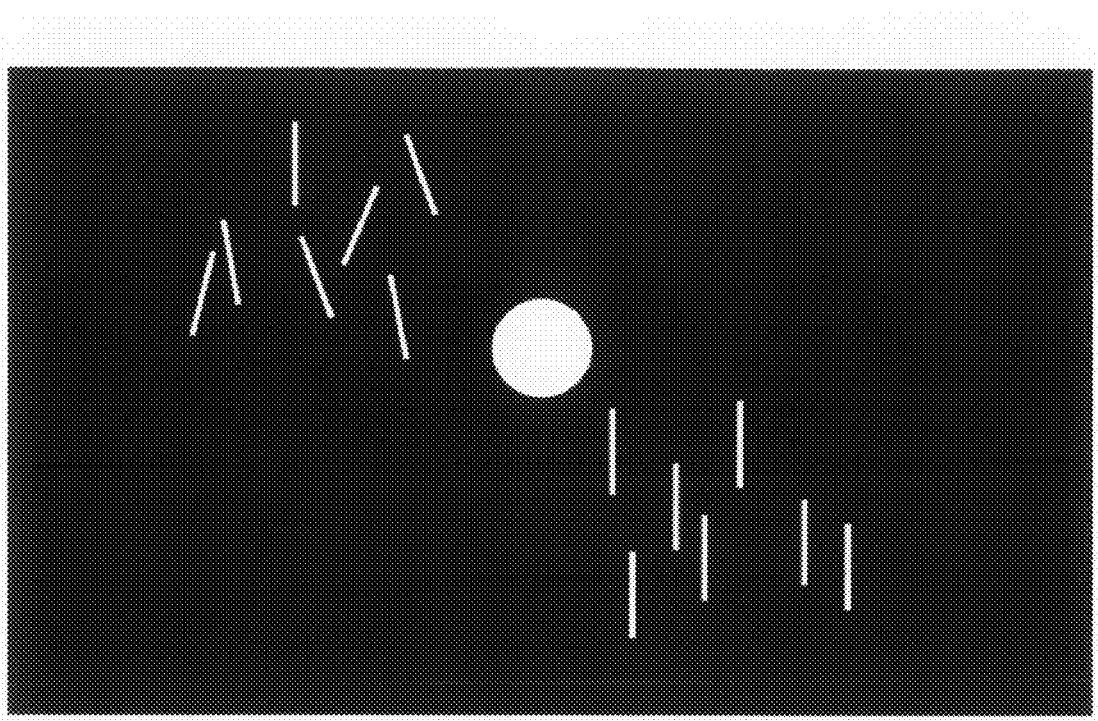
Figure 2D:
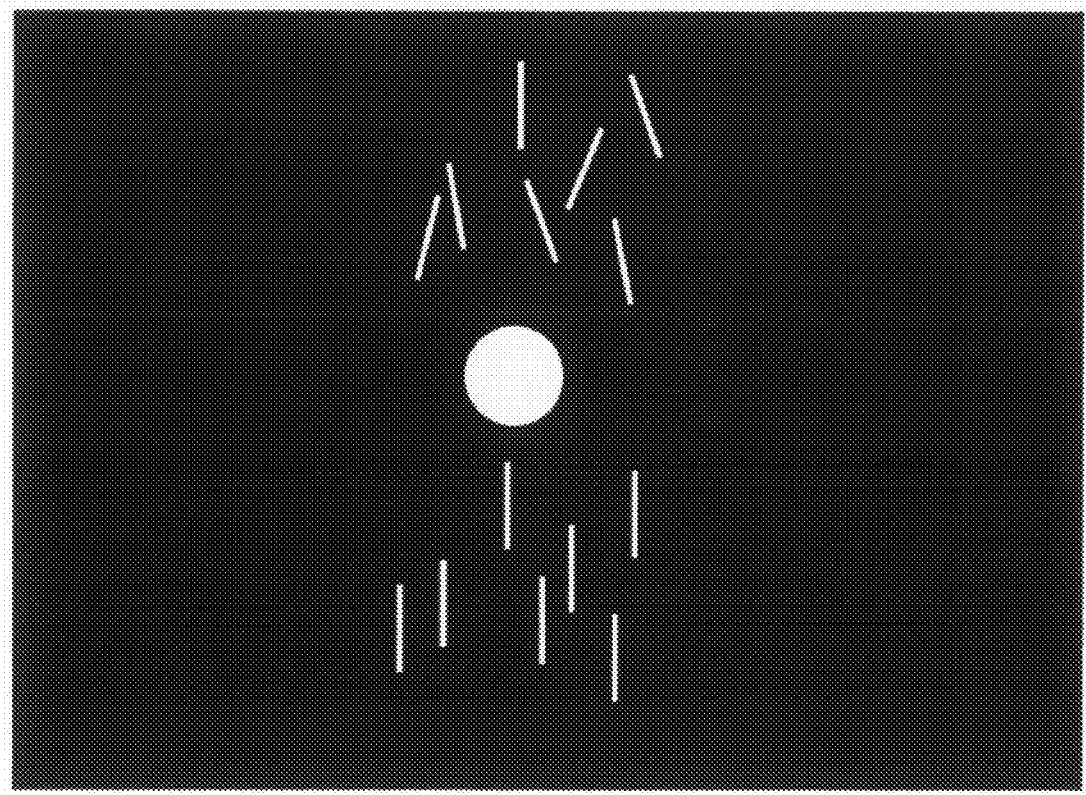

With continued reference to FIG. 1A, the program interface 120 into which input parameters are entered is depicted in FIG. 1B. The interface 120 displays entered subject information, such as name or initials 122a, age 122b and tested eye 122c. Also, the stimulus parameters are displayed. For example and without being limiting, at 124a a line number 4 is entered, at 124b a line length of 4 deg is entered, at 124c a line orientation on the 90-deg meridian is entered, and at 124d an SD of 0.4 deg is entered. In addition, the interface indicates whether the session is for the purposes of training 126. Furthermore, the interface comprises user-activated RUN 128a and QUIT 128b buttons.

In addition, the present invention provides a normative database for improved diagnostic capability and interpretation. It is contemplated that combining software analysis with the database may determine positive or negative outcome from the screening test. Alternatively or in conjunction with the normative database, outcome from the screening test may be determined by comparing a measured orientation threshold with previous thresholds obtained for a subject who is still at risk for or has a macular degenerative disease.

Furthermore, the present invention also provides a computer program product comprising a computer useable medium having a memory that tangibly stores the computer readable source code or instructions for the method for screening subjects at risk for a macular degenerative disease and which is suitable to download or transmit, including wireless transmission, over a communications network to other electronic media, such as cellular phones and PDAs. Such computer program products and memories comprising the same are well-known and standard in the art. For example, the memory may be stored on a computer having a processor effective to perform the steps stored in the memory. In addition, the computer program product stores instructions executable on an electronic media where the instructions comprise a method for analyzing the results obtained, including means for uploading or transmitting, including wireless transmission, over a communications network the test results from personal electronic media to a computer memory. Alternatively, the memory may comprise a computer diskette or memory stick or other hard storage media as are well-known in the art. Furthermore, the present invention provides the source code necessary for practice of the methods disclosed herein by one of ordinary skill in the art.

The screening methods provided herein are effective for screening for diseases of the central retina other than AMD. For example, screening may detect diabetic macular edema. Swelling in the macula leads to decreased vision and may require focal laser treatment to preserve vision based on the Early Treatment of Diabetic Retinopathy Study (ETDRS). Individuals using both eyes may not notice early changes and would benefit from the procedure and early detection.

Also, adverse drug-related reactions or drug-related macular dystrophy may be detected in the eye. Drugs to treat rheumatoid arthritis, e.g., hydroxycholoroquine, are known to have a predilection for the macula. Antipsychotic drugs, e.g., haloperidol and thioridazine, although rarely, may lead to pigmentary retinopathy. Anti-inflammatory drugs, e.g., aspirin, used in long term anticoagulant therapy may lead to maculopathy or hemorrhagic retinopathy. Antineoplastic drugs, e.g., tamoxifen, may lead to pigmentary changes, and cystoid macular edeme (CME). Hereditary macular dystrophy, such as, but not limited to, Stargardt's juvenile macular degeneration or Best's vitelliform dystrophy affect the central retina. It also is contemplated that diseases of the non-central retina, such as, hereditary peripheral retinal degenerations, e.g., retinitis pigmentosa, may be screened.

It is contemplated that the results of the screening test may, in conjunction with an eye examination by an eye care provider, may be useful in diagnosing a macular-associated disease or condition or central or peripheral retinal conditions. In addition, the screening methods and tests disclosed herein may be used as a monitoring tool for subjects testing at risk for or already having AMD or other central retinal or peripheral retinal conditions. For example, "wet" or exudative AMD produces a much more severe vision loss than "dry" AMD.

Existing therapies and those under development for exudative AMD are more effective if applied early before a substantial loss of vision occurs. It is contemplated that periodic testing at home using the screening methods provided herein may be useful to predict which eyes are likely to proceed to exudative AMD in subjects diagnosed with early AMD or to monitor the presence of macular fluid accumulation and/or retinal thickening in eyes with exudative AMD to optimize the timing of therapeutic interventions, e.g., anti-VEGF agents.

The following example(s) are given for the purpose of illustrating various embodiments of the invention and are not meant to limit the present invention in any fashion.

Example 1

Discrimination of Orientation Variability in Short Line Segments by Normal Observers Groups of randomly positioned short parallel lines frequently appear to observers with normal vision to vary in orientation. In subjects with early AMD, the added orientation variability produced by disruption of the photoreceptor layer would be expected to make the discrimination between parallel and non-parallel groups of lines more difficult. Discrimination between flashed parallel and non-parallel line segments in normal observers can be quantified.

In each trial, two groups of bright line segments were flashed sequentially within a 1 deg by 1 deg area on a dark background (FIG. 2A-2D). All of the lines in one group were parallel. In the other group, the orientation of each line in the group varied randomly from the mean orientation, e.g., horizontal, according to a pre-determined angular standard deviation (SD). Each group of lines was flashed for 200 ms to prevent scanning eye movements. Using the method of constant stimuli, the SD of the added orientation variability that observers could just discriminate from lines that were physically parallel was determined.

The threshold value of the orientation SD decreases by approximately four fold as the length of the line segments increases from 0.1 to 0.4 deg. Thresholds are nearly independent of the line density (range 2-10 lines/deg sq) and mean orientation, and increase only 10-25% when the lines are viewed with +0.50 or +1.00 D blur, to simulate small degradations of visual acuity. Presentation of 0.4 deg lines at an eccentricity of 1 deg also produces a 25% increase in the orientation SD threshold.

Normal orientation-SD thresholds are relatively independent of stimulus parameters except for line length and are relatively unaffected by conditions that slightly reduce visual acuity. Because random line segments are not susceptible to filling in, orientation SD thresholds should be sensitive to early retinal changes in subjects with AMD that generate variability in the representation of stimulus orientation.

Example 2

Orientation Discrimination for Randomly Positioned Line Segments in Subjects At-Risk for Developing or Having Early AMD 17 eyes of 11 subjects with healthy maculae and 25 eyes of 15 subjects at-risk for early AMD were tested. At-risk eyes were identified by the presence of macular drusen and/or early RPE changes, as determined from digital fundus photographs by a masked examiner. Normal subjects varied in age from 52-79 (median=65 years) and at-risk subjects varied in age from 58-82 (median=69 years). Best-corrected visual acuity ranged from 20/15-20/30 (median=20/20) in the normal subjects and from 20/15-20/40+1 (median=20/20) in the at-risk group.

To assess orientation discrimination, subjects viewed two 1-deg patches that contained 0.4-deg lines (FIGS. 2A-2D). Each pair of patches was presented for 200 ms and straddled a fixation spot along one of 4 meridians. In one randomly selected patch the lines were parallel and in the other patch the orientation of each line varied randomly from the mean orientation with a pre-determined angular standard deviation. After each presentation subjects indicated in which patch the lines appeared more parallel. The orientation threshold was determined from a psychometric function, fit to the responses to 80 trials. Amsler grid testing and automated 10-2 perimetry were performed also for each eye.

Figure 3A:
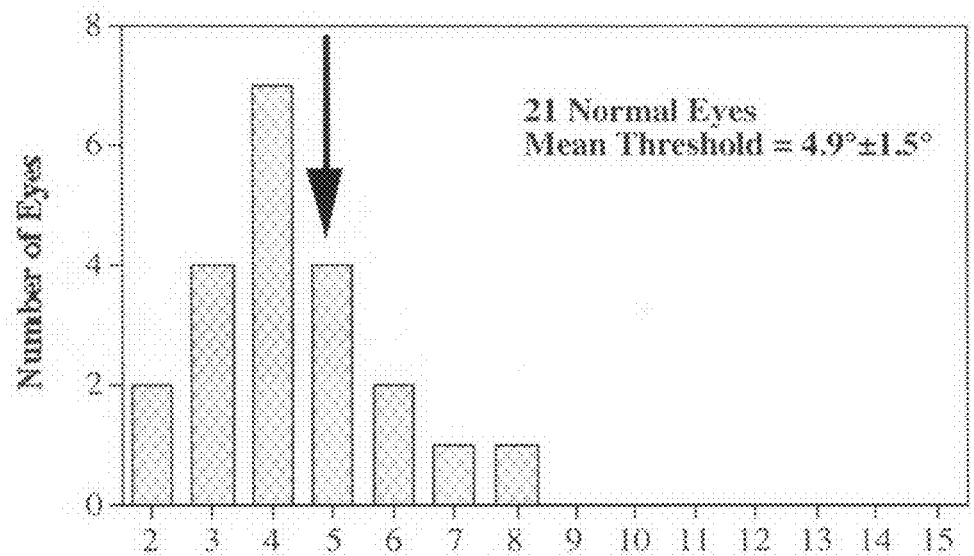
FIGS. 3A-3B show the distribution of orientation thresholds for 21 normal eyes (FIG. 3A) and 29 eyes judged to be at risk for early AMD (FIG. 3B). All eyes have better than 20/40 acuity. SD is in deg.
Figure 3B:
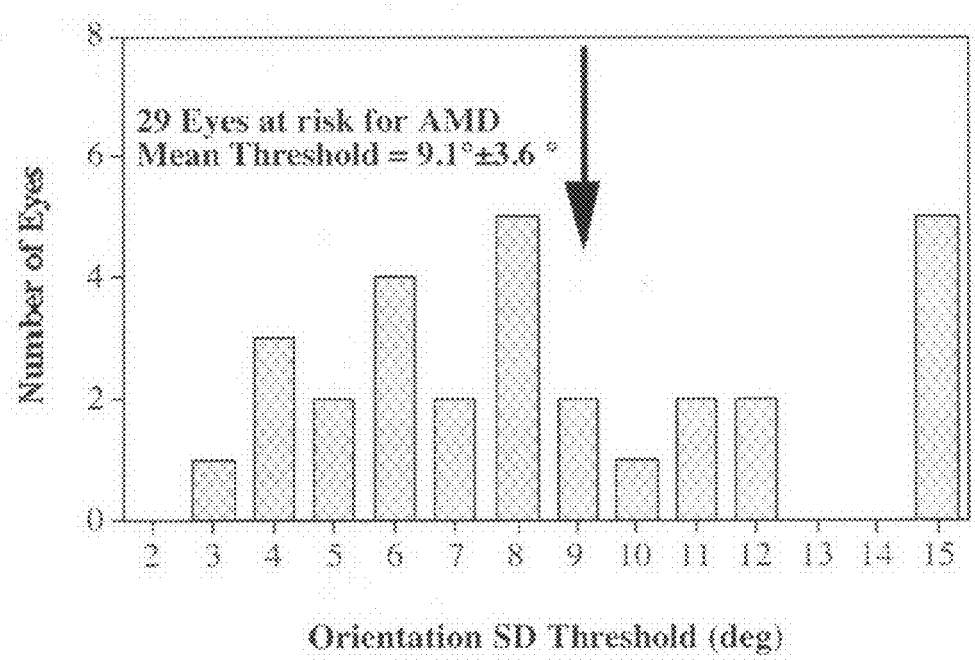

Average orientation thresholds were nearly twice as high in at-risk compared to normal eyes ($9.1 \pm 3.6$ deg vs. $4.9 \pm 1.5$ deg; p=1.9e-6) (FIGS. 3A-3B). Thresholds in 17 of the 29 at-risk eyes were higher than 95% of the normal eyes. Response errors were distributed non-uniformly by target meridian in 9 of the at-risk eyes, suggesting that retinal disruption was de-centered with respect to the fovea. In contrast, none of the normal eyes showed a non-uniform distribution of errors. Amsler grid responses were abnormal in 2 at-risk eyes and 1 normal eye. Central field defects ($p<0.01$) with 10-2 perimetry occurred with equal probability (20%) in the at-risk and normal eyes. In contrast to Amsler grid and automated central-field testing, psychophysical orientation discrimination distinguishes between eyes with and without subtle age-related macular changes. Despite the narrow range of visual acuities in the tested eyes, orientation sensitivity correlated significantly with visual acuity ($r=0.54$, $p=0.02$), but only in the eyes that were judged to be at risk for early AMD.

Example 3

Figure 4A:
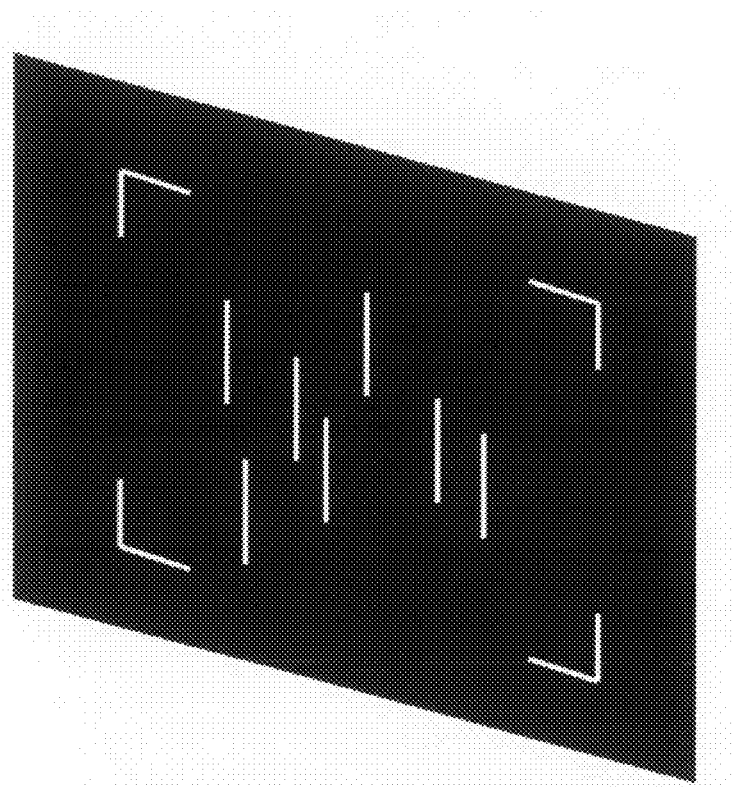
FIGS. 4A-4B depict targets with fixation brackets of random parallel (FIG. 4A) and random non-parallel (FIG. 4B) lines to assess orientation discrimination when presented sequentially.
Figure 4B:
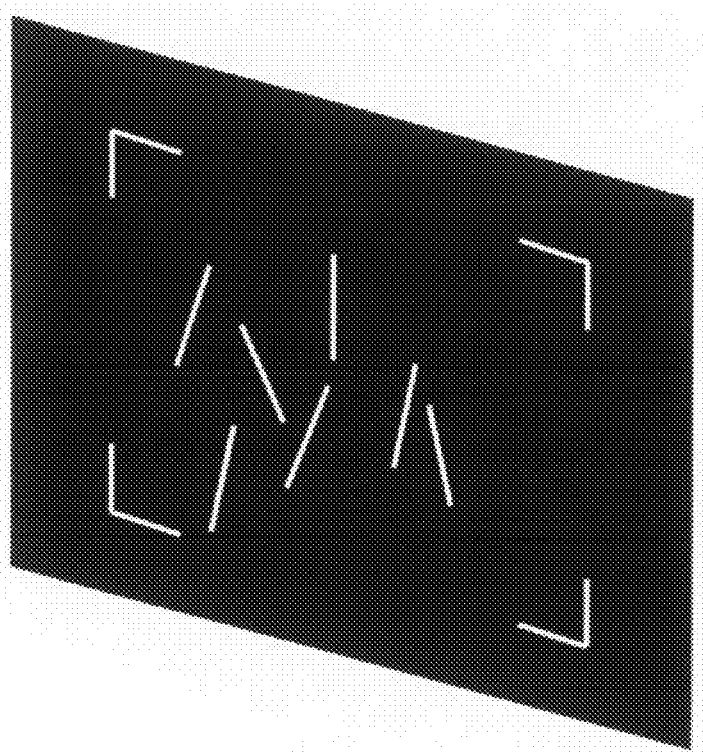

Discrimination of Orientation Variability in Short Line Segments by Observers Having Exudative AMD Participants are beginning intravitreal anti-VEGF injections. e.g., bevacizumab or ranubizimab, to treat macular fluid that results from choroidal neovascularization. The test of orientation discrimination uses the following protocols differing from those in Example 2. First, sets of parallel and non-parallel line segments are presented sequentially (FIGS. 4A-4B). Second, the length of the randomly positioned line segments is 0.6 deg and the number of line segments in each presentation is 10. Third, each presentation is centered within the same 4-deg central region of the field, rather than offset along different visual-field meridians. Fourth, fixation is directed between a set of 4 peripherally located brackets. Fifth, the total number of trials per eye is approximately 20 and an adaptive psychophysical method is used (12-13).

Within one trial, each set of lines is presented for 200 ms to prevent scanning eye movements. A 1-s interval between each pair of presentations allows the observer to resume fixation before the next set of lines is presented. A larger number of longer lines is selected to increase their visibility to those observers with advanced AMD. Because test performance does not depend on the number of lines, the results should not be affected even if some of the lines are not completely visible. Lines are presented within a 4 deg area because this roughly matches the size of the retinal region, i.e., ±500 microns, used to calculate center-point macular thickness from OCT data (14). An adaptive psychophysical method allows orientation-discrimination thresholds to be determined precisely using a much smaller number of trials. Sequential, rather than simultaneous presentations (Example 1) of line segments were used and orientation discrimination thresholds in normal eyes that are similar to those shown in FIG. 3A above were obtained (15).

The principal comparisons are between measured orientation discrimination and center-point macular thickness. Also, categories for the distribution of fluid in macular OCT images are assessed. Changes in orientation sensitivity are compared to changes in center point thickness, as defined relative to the measures obtained on the initial testing day. It is contemplated that both quantitative and qualitative indices of structural macular integrity correlate highly with measured orientation discrimination. Secondary analyses compare both OCT indices and orientation discrimination to visual acuity and to perceptual distortions, as determined qualitatively from the Amsler grid. It is also contemplated that center-point thickness will correlate with visual acuity. It is further contemplated that a similar correlation is observed between orientation discrimination and visual acuity, as demonstrated in Example 2 for early AMD. However, because of the insensitivity of Amsler grid testing to retinal defects, little correlation should be observed between the Amsler-grid results and either orientation discrimination or indices based on the OCT images.

The following references are cited herein.
1. Takeda et al. (2007) Brit. J. Opthalmol. 91:1177-1182.
2. Zarbin, M. & Szirth, B. (2007) Optom. Vision Sci. 84:559-572.
3. Brown, D. M. & Regillo, C. D. (2007) Am. J. Opthalmol. 144:627-637.
4. Fung et al. (2007) Am. J. Opthalmol. 143:566-583.
5. Fine et al. (1986) Arch. Opthalmol. 104:513-514.
6. Schuchard, R. A. (1993) Arch. Opthalmol. 111:776-780.
7. Achard et al. (1995) Am. J. Opthalmol. 120:322-329.
8. Ramachandran, V. S. (1992) Amer. 266:44-49.
9. Zur, D. & Ullman, S. (2003) Vision Res. 43:971-982.
10. Preferential Hyperacuity Perimetry Study Group. (2005) Am. J. Opthalmol. 112:1758-1765.
11. Preferential Hyperacuity Perimetry Study Group. (2007) Retina 25:296-303.
12. Leek, M. R. (2001) Percept. Psychophys. 63:1279-1292.
13. Anderson A. A. & Johnson, C. A. (2006) Vision Res. 46:2403-2411.
14. Bressler, N. M. & Ahmed, I. I. K. (2006) Essential OCT. Carl Zeiss Meditec, Dublin, Calif.
15. Lennon et al. (2005) Optom. Vision Sci. 82: E-abstract #055234.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages inherent herein. The present examples, along with the methods, procedures, systems, and/or applications described herein are presently representative of preferred embodiments, are exemplary and are not intended as limitations on the scope of the invention. Changes therein and other uses will occur to those skilled in the art which are encompassed within the spirit of the invention as defined by the scope of the claims.

What is claimed is:

1. A system for screening for a retinal-associated eye disease in a subject, comprising:
   a surface configured to display at a location thereon a pair of targets including a first target of a plurality of parallel lines and a second target of a plurality of non-parallel lines to a subject;
   a memory; and
   a processor connected to the memory and configured to perform the steps of:
   (a) displaying at a location on a surface a pair of targets including a first target of a plurality of parallel lines and a second target of a plurality of non-parallel lines to a subject;
   (b) selecting a target in which the lines appear to be more parallel by the subject;
   (c) calculating an orientation discrimination threshold for the subject based on the selections; and
   (d) correlating an increase in the orientation discrimination threshold in the subject compared to an orientation discrimination threshold of a control.

2. The system of claim 1, further comprising one or both of a normative database of orientation discrimination thresholds as the normal control or a listing of previous thresholds measured for the subject stored in the memory.

3. The system of claim 1, further comprising a communication network connection, wherein the processor is configured to perform further steps of:
   transmitting the subject's selections to another processor.

4. The system of claim 3, wherein the transmissions are in real time.

5. The system of claim 4, wherein the subject's selections are transmitted to an eye care provider in real time.

6. The system of claim 2, further comprising a communication network connection, wherein the processor is configured to perform further steps of:
   transmitting times at which the subject performs the steps (a) to (c) to another processor.

7. The system of claim 2, further comprising a communication network connection, wherein the processor is configured to perform further steps of:
   receiving a reminder for the subject to perform steps (a) to (c) as instructed by an eye care provider.

8. The system of claim 1, wherein the first target and the second target are displayed simultaneously or sequentially.

9. The computer program product of claim 1, wherein the retinal-associated eye disease is a disease of the macula, of the central retina or of the peripheral retina.

10. The method of claim 1, wherein the retinal-associated eye disease is early age-related macular degeneration, diabetic macular edema, hereditary macular dystrophy, drug-related macular dystrophy, hereditary peripheral retinal degenerations, pigmentary retinopathy, or cystoid macular edema.

11. A program storage device readable by an electronic medium and tangibly storing instructions executable by the electronic medium to perform the steps for screening for a retinal-associated eye disease in a subject, comprising:
   (a) displaying at a location on a surface a pair of targets including a first target of a plurality of parallel lines and a second target of a plurality of non-parallel lines to a subject;
   (b) selecting a target in which the lines appear more to be parallel by the subject;
   (c) calculating an orientation discrimination threshold for the subject based on the selections; and
   (d) correlating an increase in the orientation discrimination threshold in the subject compared to an orientation discrimination threshold of a control.

12. The program storage device of claim 11, further storing a normative database of orientation discrimination thresholds as the normal control or a listing of previous thresholds measured for the subject as the control.

13. The program storage device of claim 11, wherein the executable instructions further perform the steps of:
   transmitting the subject's selections to another electronic medium.

14. The program storage device of claim 13, wherein the transmissions are in real time.

15. The program storage device of claim 11, wherein the executable instructions further perform the steps of:
   transmitting times at which the subject performs the steps (a) to (c) to another electronic medium.

16. The program storage device of claim 15, wherein the executable instructions further perform the steps of:
   receiving a reminder for the subject to perform steps (a) to (c) as instructed by an eye care provider.

17. The program storage device of claim 11, wherein the electronic medium is a computer, a cellular phone, a PDA or a self-contained electronic device.

18. The program storage device of claim 11, wherein the first target and the second target are displayed simultaneously or sequentially.

19. A computer program product comprising a computer useable medium that tangibly stores as computer readable code executable instructions to perform method steps to:
   (a) display at a location on a surface a pair of targets including a first target of a plurality of parallel lines and a second target of a plurality of non-parallel lines to a subject;
   (b) calculate an orientation discrimination threshold for the subject based on the subject's selection of target in which the lines appear to be more parallel; and
   (c) correlate an increase in the orientation discrimination threshold in the subject compared to an orientation discrimination threshold of a control as indicating a risk for the retinal-associated eye disease in the subject.

20. The computer program product of claim 19, the executable instructions performing a further method step to:
   transmit the subject's selections over a communication network.

21. The computer program product of claim 20, wherein the transmissions are in real time.

22. The computer program product of claim 19, the executable instructions performing a further method step to:
   transmit the subject's selections over a communication network in real time to an eye care provider.

23. The computer program product of claim 19, the executable instructions performing a further method step to:
   transmit over the communication network times at which the subject performs the steps (a) to (c).

24. The computer program product of claim 19, the executable instructions performing a further method step to:
   send a reminder to the subject to perform the steps (a) to (c) as instructed by an eye care provider.

25. The computer program product of claim 19, wherein the surface comprises a computer monitor screen, a screen on a cellular phone, a screen on a PDA or a screen on a self-contained electronic device.

26. The computer program product of claim 19, wherein the control is a normal control comprising a normative database of orientation discrimination thresholds determined for normal eyes or comprises previous thresholds measured for the subject.

27. The computer program product of claim 19, wherein the targets are displayed simultaneously or sequentially.

28. The computer program product of claim 19, wherein the targets are displayed for 200 ms or less.

29. The computer program product of claim 19, wherein the targets are displayed on the surface at 8 visual-field locations adjacent to a central fixation stimulus or the targets are displayed centered within a same central region of a visual-field such that fixation is directed between a set of 4 peripherally located brackets.

30. The computer program product of claim 19, wherein the lines are about 0.2 deg to about 0.6 deg in length.

\* \* \* \* \*